United States Patent [19]

Takahashi et al.

[11] Patent Number: 5,007,406
[45] Date of Patent: Apr. 16, 1991

[54] BENDING CONTROL DEVICE OF ENDOSCOPE

[75] Inventors: Nagashige Takahashi; Teruo Ouchi, both of Tokyo, Japan

[73] Assignee: Asahi Kogaku Kogyo Kabushiki Kaisha, Tokyo, Japan

[21] Appl. No.: 429,006

[22] Filed: Oct. 30, 1989

[30] Foreign Application Priority Data

Nov. 4, 1988 [JP] Japan ................. 63-280061
Nov. 4, 1988 [JP] Japan ................. 63-280062

[51] Int. Cl.⁵ ............................................ A61B 1/00
[52] U.S. Cl. ............................................ 128/4
[58] Field of Search ............................................ 128/4

[56] References Cited

U.S. PATENT DOCUMENTS

| | | | |
|---|---|---|---|
| 4,078,555 | 3/1978 | Takahashi | 128/4 |
| 4,462,282 | 7/1984 | Ouchi et al. | 128/4 |
| 4,617,914 | 10/1986 | Ueda | 128/4 |
| 4,742,816 | 5/1988 | Suzuki et al. | 128/4 |
| 4,762,119 | 8/1988 | Allred, III et al. | 128/4 |

Primary Examiner—William H. Grieb
Attorney, Agent, or Firm—Sandler, Greenblum & Bernstein

[57] ABSTRACT

A bending control device of an endoscope for bending a bendable portion, formed at the distal end of the insert part of the endoscope, by manual operation of a control part connected to the proximal end of the insert part is provided. The bending control device has an up and down bending control knob rotatably and detachably provided on the control part to control bending of the bendable portion in upward and downward directions. A right and left bending control knob is rotatably and detachably provided on the control part, in coaxially superposed relation to the up and down bending control knob, to control bending of the bendable portion in the rightward and leftward directions. An attaching and removing device is also provided for manually attaching and removing the two bending control knobs to and from the control part. Thus, the bending control knobs can be removed from the control part as desired for washing and disinfection or replacement with new bending control knobs.

15 Claims, 5 Drawing Sheets

BENDING CONTROL DEVICE OF ENDOSCOPE

BACKGROUND OF THE INVENTION

1. Field of the Invention

The present invention relates to a bending control device of an endoscope and, more particularly, to a structure of a bending control knob section provided on the control part of an endoscope.

2. Description of the Related Art

In the bending control device of a typical conventional endoscope, an up and down bending control knob (hereinafter referred to as a U-D bending control knob) and a right and left bending control knob (hereinafter referred to as an R-L bending control knob) are coaxially superposed on the control part of the endoscope. Each bending control knob is individually attached to a bending control mechanism in the control part by the use of by, for example, fine screw or a nut.

The prior art suffers, from the following problems. Since each bending control knob is installed by use of a screw or a nut, a screwdriver or a special-purpose tool must be used to attach or remove the control knobs. It is therefore impossible for a doctor to readily change the bending control knobs of the endoscope. It may be necessary to replace the control know with a differently shaped knob depending on the situation or depending on the preference of the doctor using the endoscope. In addition, may be necessary to remove a bending control knob to wash and disinfect it after use since contaminative matter, for example, mucus or blood, may attach to the knob.

Further, since the two bending control knobs must individually be attached or removed using a screwdriver or a special-purpose tool, a complicated and time-consuming operation is needed to replace the control knobs leaving the user (doctor) with considerably troublesome work.

In a conventional bending control device, each bending control knob is detachably provided with an adapter which is larger in size than the control knob. However, it is considerably complicated and troublesome to attach adapters to the two bending control knobs or remove the adapters therefrom. Further since the bending control knobs themselves are not removed, it remains difficult to remove them for washing and disinfection.

In general, the doctor, when handling an endoscope having a control part with two coaxially superposed control knobs, holds the control part with his left hand and operates the control knobs with his right hand. Depending on the situation, the doctor uses either his right hand or the thumb of his left hand to turn the control knobs.

Accordingly, the conventional bending control device of the type having coaxially superposed control knobs on the control part has the disadvantage that contaminative matter is transferred from the right hand, contaminated by contacting the insert part which may have been inserted into a hollow organ of the patient's body to the left hand via the bending control knobs. The results in the whole control part being contaminated. Therefore, it is necessary to disinfect or sterilize the control part by dipping it in a disinfectant or sterilant before each use. This endoscope disinfecting operation is extremely complicated and time-consuming. Since at least 30 minutes is needed to complete each single disinfection, another endoscope must be used for examination of the next patient, and it is therefore necessary to prepare a plurality of endoscopes in order to conduct examination of a large number of patients.

If the disinfection or sterilization of the control part is insufficient, there is a fear that bacteria and viruses may be transmitted from one patient to another through the contaminated control part.

SUMMARY OF THE INVENTION

An object of the present invention is to provide a bending control device of an endoscope which is designed so that the two bending control knobs can be readily removed from the control part for washing and disinfection, or replacement at any desired time.

Another object of the present invention is to provide a bending control device of an endoscope which is designed so that there is no fear of the control part being contaminated through the bending control knobs and also so that contaminated portions can readily be disinfected.

Other objects and advantages of the present invention will become apparent from the following detailed description of illustrated embodiments of the invention.

According to the present invention, there is provided a bending control device for an endoscope for bending a bendable portion, formed at the distal end of the insert part of the endoscope, by manual operation of a control part connected to the proximal end of the insert part. The control device comprises: an up and down bending control knob rotatably and detachably provided on the control part to control bending of the bendable portion in upward and downward directions. A right and left bending control knob rotatably and detachably provided on the control part, in coaxially superposed relation to the up and down bending control knob, to control bending of the bendable portion in rightward and leftward directions. An attaching and removing device for manually attaching and removing the two bending control knobs to and from the control part is also provided.

In addition, there is provided a bending control device of an endoscope for bending a bendable portion formed at the distal end of the insert part of the endoscope. The bending of the bendable portion is controlled by a manual operation of a control part connected to the proximal end of the insert part, comprising: at least one up and down bending control knob rotatably provided on the control part to control bending of the bendable portion in upward and downward directions; at least one right and left bending control knob rotatably provided on the control part, in coaxially superposed relation to the up and down bending control knob, to control bending of the bendable portion in rightward and leftward directions; and a partition device having a larger outer diameter than that of the up-and-down and right-and-left bending control knobs, the partition device being disposed closer to the control part than the one of the bending control knobs that is farthest from the control part, thereby isolating the space at the side of the partition device which is closer to the control part from the space at the other side of the partition device.

BRIEF DESCRIPTION OF THE DRAWINGS

The present invention may be more fully understood from the description of preferred embodiments of the invention set forth below, together with the accompanying drawings, in which.

DESCRIPTION OF THE EMBODIMENTS

Figure 1:
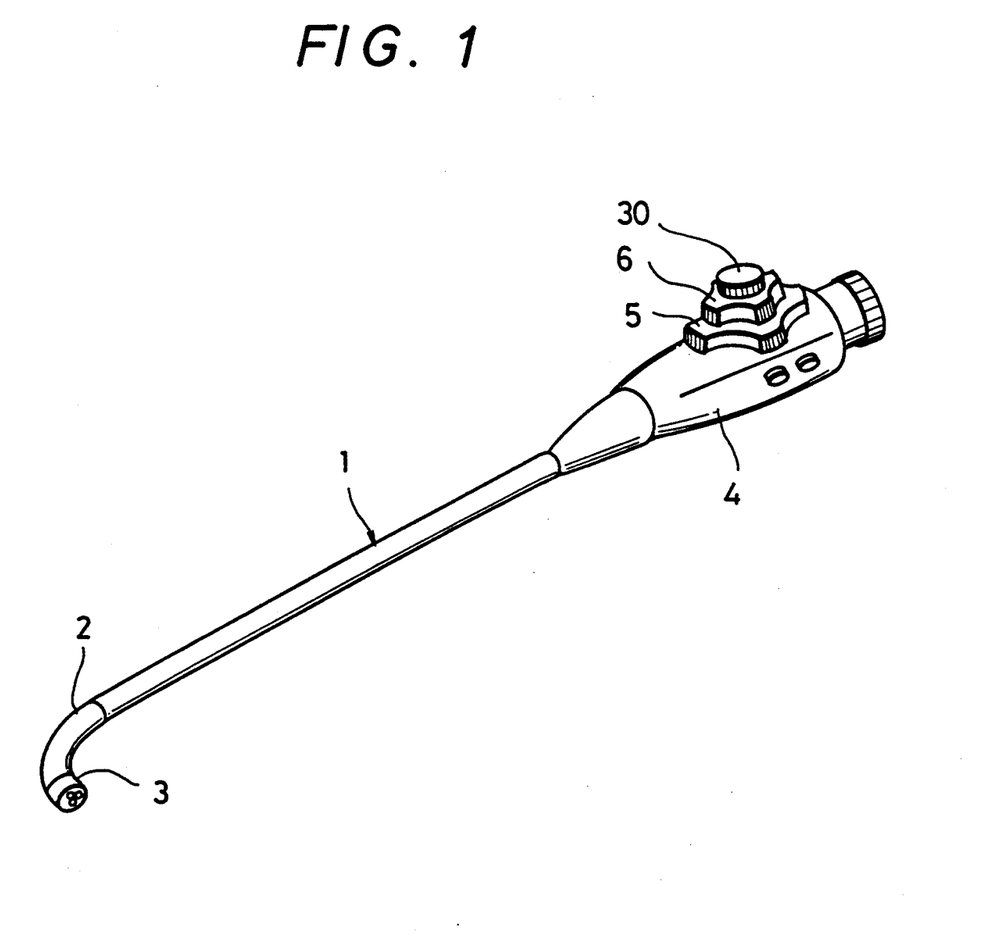
FIG. 1 is a perspective view showing the general arrangement of an endoscope according to a first embodiment of the present invention.

Referring to FIG. 1, which shows the general arrangement of an endoscope according to a first embodiment of the present invention, the reference numeral 1 denotes an insert part which is sheathed with a flexible tube. At the distal end of the insert part 1 is formed a bendable portion 2 which is capable of bending in any direction, that is, upward, downward, rightward, leftward and other directions. A distal end part 3 incorporating an objective optical system is coupled to the distal end of the bendable portion 2.

A control part 4 is connected to the proximal end of the insert part 1. A U-D bending control knob 5 and an R-L bending control knob 6 are coaxially superposed on the control part 4.

Figure 2:
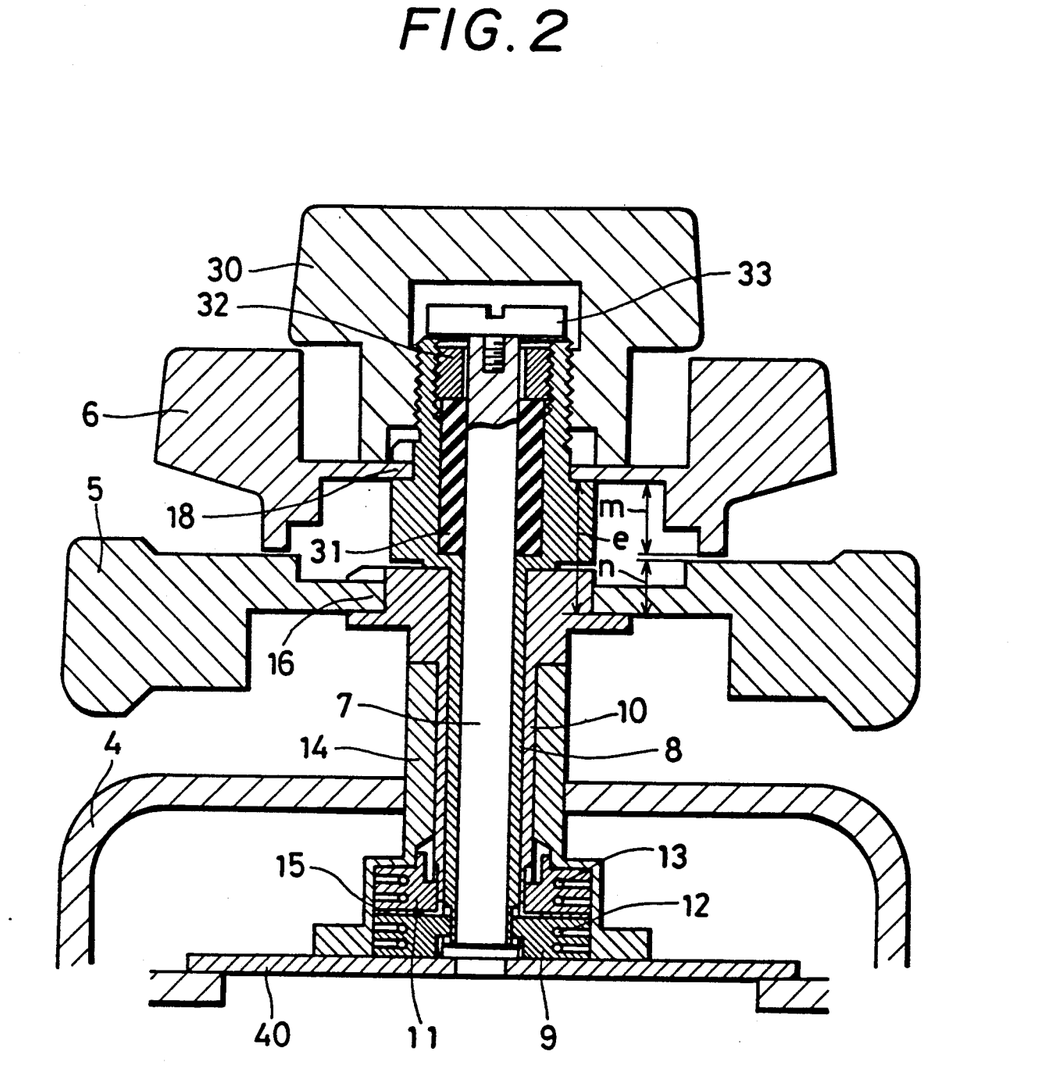
FIG. 2 is a sectional view of a bending control device according to the first embodiment.

FIG. 2 shows a bending control device according to the first embodiment. A base 40 is secured in the control part 4, and a fixed shaft 7 is fixed to the base 40 so as to project outside the control part 4. An R-L rotary shaft 8 for right and left bending control is rotatably fitted on the fixed shaft 7. An R-L pulley 9 for right and left bending control is engaged with the proximal end portion of the R-L rotary shaft 8 so that the pulley 9 rotates together with the rotary shaft 8 in one unit. A U-D rotary shaft 10 for up and down bending control is rotatably fitted on the outer periphery of the R-L rotary shaft 8. A U-D pulley 11 for up and down bending control is engaged with the proximal end portion of the U-D rotary shaft 10 so that the pulley 11 rotates together with the rotary shaft 10 in one unit. The reference numeral 15 denotes a washer-shaped spacer.

The proximal end portions of control wires 12 and 13 are wound around the pulleys 9 and 11, respectively, the distal ends of the control wires 12 and 13 being connected to the bendable portion 2, so that, as the pulleys 9 and 11 rotate, the control wires 12 and 13 are pulled and the bendable portion 2 is thereby bent. The reference numeral 14 denotes a cover which serves as a bearing for the U-D rotary shaft 10 and which also prevents the control wires 12 and 13 from bulging out of the respective pulleys 9 and 11.

The outer end portion of the U-D rotary shaft 10 has a relatively large outer diameter to define a large-diameter portion. The upper half of the large-diameter portion has a non-circular (e.g., square) cross-sectional configuration. The U-D bending control knob 5 is fitted onto the upper half of the large-diameter portion from the outer side and thus engaged therewith. The reference numeral 16 denotes the engagement portion of the control knob 5. The configuration of the bore that is formed in the center of the U-D bending control knob 5 is coincident with the non-circular cross-sectional configuration of the U-D rotary shaft 10. Accordingly, the U-D bending control knob 5 rotates together with the U-D rotary shaft 10 in one unit, but the control knob 5 can be removed from the U-D rotary shaft 10 by pulling it outward (i.e., upward as viewed in FIG. 2) along the axis of rotation of the knob 5.

Similarly, the R-L bending control knob 6 rotates together with the large-diameter portion of the R-L rotary shaft 8, which is formed outward of the U-D rotary shaft 10, through a non-circular (e.g., square) engagement portion 18 of the control knob 6, but the knob 6 can be removed by pulling it outward along the axis of rotation of the knob 6.

It should be noted that the bending control knobs 5 and 6 are formed so that the distance e between the bottoms of the engagement portions 16 and 18 is slightly greater than the sum of the thicknesses m and n of those portions of the control knobs 5 and 6 which are disposed in the area between the bottoms of the engagement portions 16 and 18. Accordingly, when the bending control knobs 5 and 6 are in engagement with the respective engagement portions 16 and 18, the bending control knobs 5 and 6 can rotate independently of each other with no interference and substantially no play.

A clamping knob (attaching and removing means) 30 is in thread engagement with the head portion of the R-L rotary shaft 8, the knob 30 projecting upward beyond the outer end of the R-L bending control knob 6 so that the knob 30 can be rotated by hand. By manually tightening the clamping knob 30, the R-L bending control knob 6 is pressed from the outer side and thereby secured to the R-L rotary shaft 8. Thus, the U-D bending control knob 5 is simultaneously secured to the U-D rotary shaft 10. If the clamping knob 30 is untightened by hand and removed from the R-L rotary shaft 8, both the bending control knobs 5 and 6 can be pulled outward and thus removed from the control part 4. Accordingly, the two bending control knobs 5 and 6 can be attached to or removed from the control part 4 by tightening or untightening the clamping knob 30 by hand.

A resilient friction member 31 is loaded within the large-diameter portion at the top of the R-L rotary shaft 8 in a compressed state between the rotary shaft 8 and the fixed shaft 7. Accordingly, as the R-L rotary shaft 8 rotates, frictional resistance occurs between the same and the fixed shaft 7. Therefore, the R-L bending control operation is conducted while being braked with a predetermined level of frictional force at all times. The degree to which the resilient friction member 31 is compressed can be adjusted by varying the degree to which a nut 32 is screwed into the outer end portion of the R-L rotary shaft 8.

The reference numeral 33 denotes a bolt screwed into the top portion of the fixed shaft 7 to prevent the R-L rotary shaft 8 from coming off.

According to the present invention, both the U-D and R-L bending control knobs can be simultaneously attached or removed by manually actuating a single attaching and removing means. It is therefore possible for the doctor to remove both the bending control knobs from the control part with ease for washing and disinfection or replacement.

Figure 3:
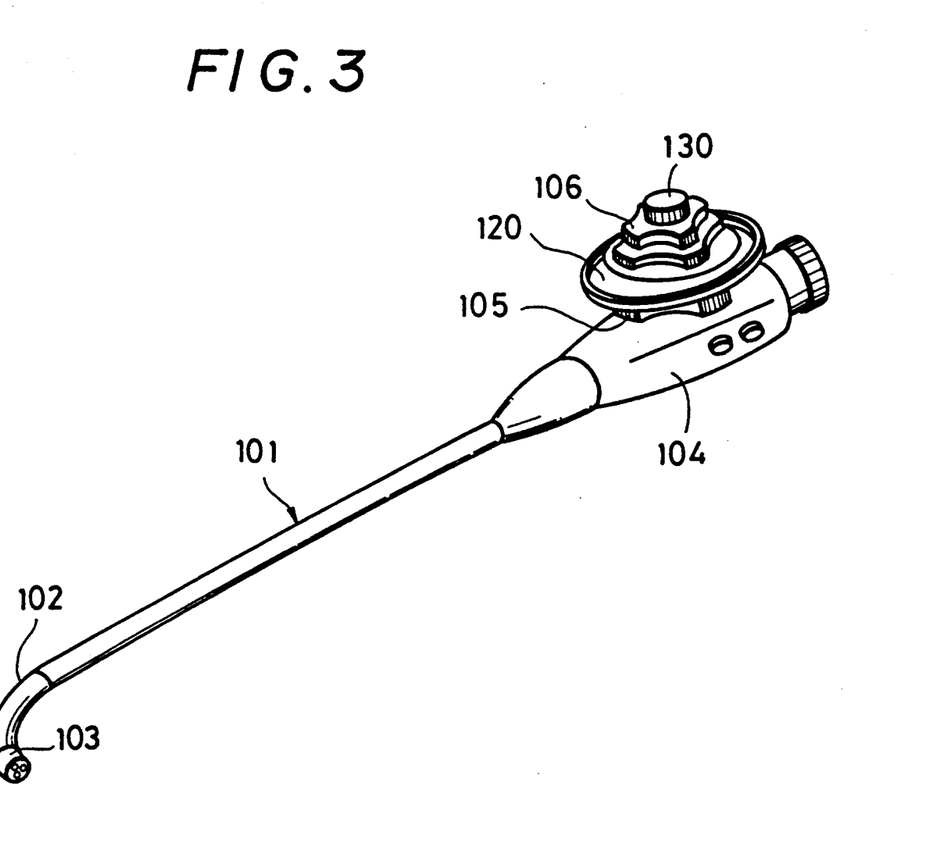
FIG. 3 is a perspective view showing the general arrangement of an endoscope according to a second embodiment of the present invention.
Figure 4:
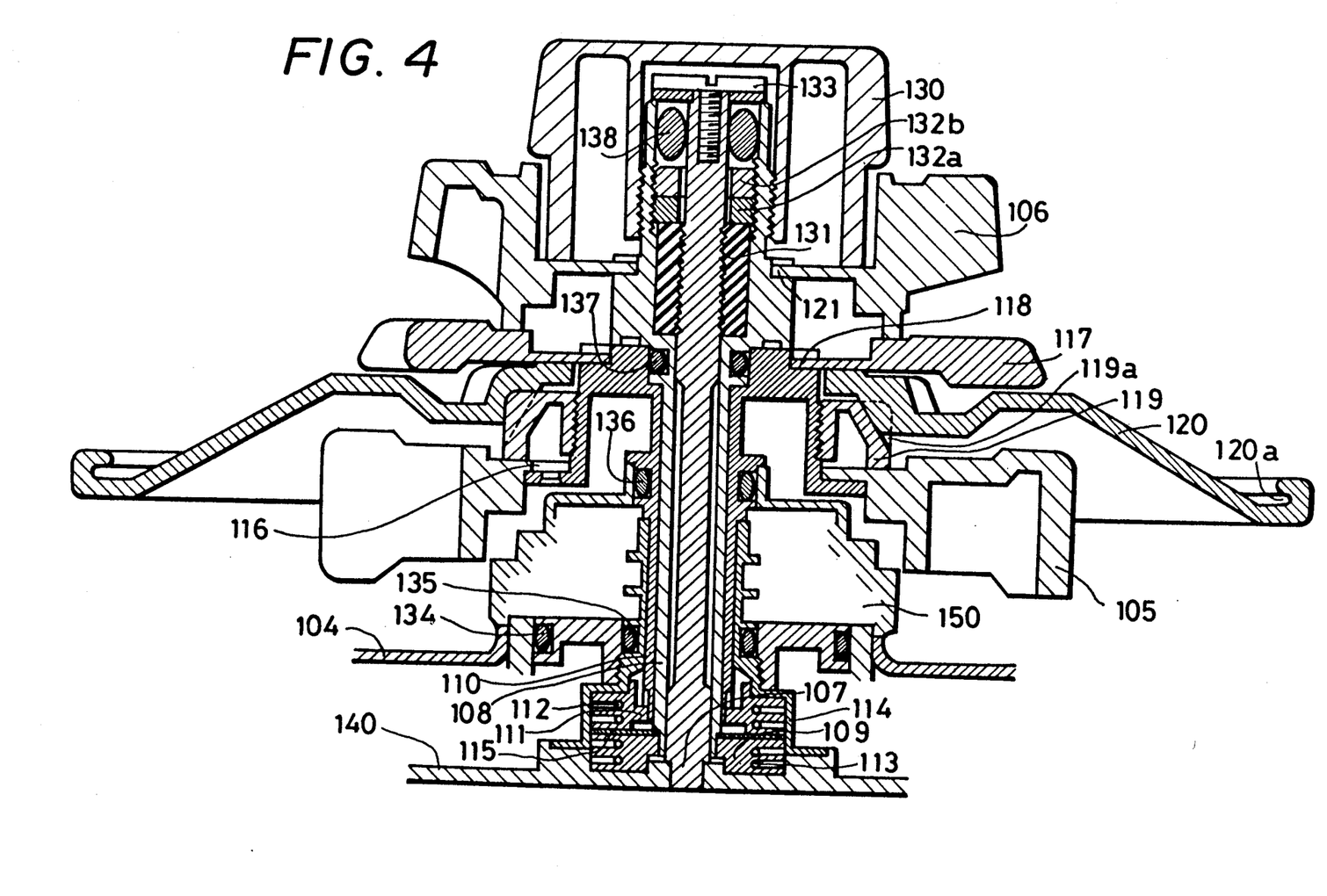
FIG. 4 is a sectional view of a bending control device according to the second embodiment.
Figures 5, 6, 7:
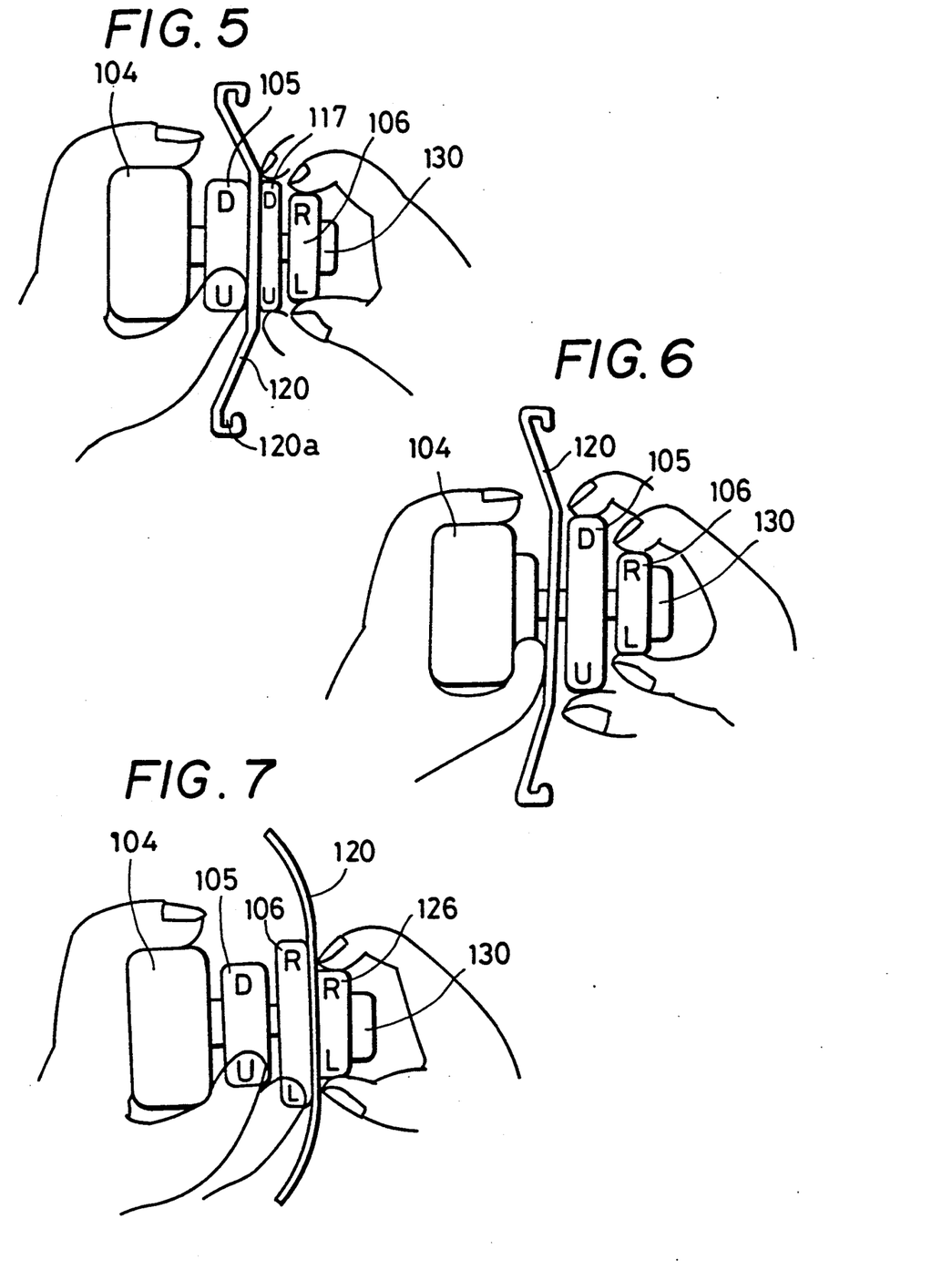
FIG. 5 schematically shows the external appearance of the bending control device of the second embodiment.
FIG. 6 schematically shows the external appearance of a bending control device of a third embodiment of the present invention.
FIG. 7 schematically shows the external appearance of a bending control device of a fourth embodiment of the present invention.

FIGS. 3 to 5 show in combination a second embodiment of the present invention, in which FIG. 3 shows the general arrangement of an endoscope according to the second embodiment. The reference numeral 101 denotes an insert part which is sheathed with a flexible tube. At the distal end of the insert part 101 is formed a bendable portion 102 which is capable of bending in any direction, that is, upward, downward, rightward, leftward and other directions. A distal end part 103 incorporating an objective optical system is coupled to the distal end of the bendable portion 102. A control part 104 is connected to the proximal end of the insert part 101. A U-D bending control knob 105 and an R-L bending control knob 106 are coaxially superposed on the control part 104.

FIG. 4 shows a bending control device according to the second embodiment. A base 140 is secured in the control part 104, and a fixed shaft 107 is fixed to the base 140 so as to project outside the control part 104. An R-L rotary shaft 108 for right and left bending control is rotatably fitted on the fixed shaft 107. An R-L pulley 109 for right and left bending control is engaged with the proximal end portion of the R-L rotary shaft 108 so that the pulley 109 rotates together with the rotary shaft 108 in one unit. A U-D rotary shaft 110 for up and down bending control is rotatably fitted on the outer periphery of the R-L rotary shaft 108. A U-D pulley 111 for up and down bending control is engaged with the proximal end portion of the U-D rotary shaft 110 so that the pulley 111 rotates together with the rotary shaft 110 in one unit. The reference numeral 115 denotes a washer-shaped spacer.

The proximal end portions of control wires 112 and 113 are wound around the pulleys 109 and 111, respectively, the distal ends of the control wires 112 and 113 being connected to the bendable portion 102, so that, as the pulleys 109 and 111 rotate, the control wires 112 and 113 are pulled and the bendable portion 102 is thereby bent. The reference numeral 114 denotes a cover which serves as a bearing for the U-D rotary shaft 110 and which also prevents the control wires 112 and 113 from bulging out of the respective pulleys 109 and 111.

The U-D rotary shaft 110 has a flange provided outside the control part 104 and at the middle of the bending control knob section, the flange being provided with a rivet 116 which is to be fitted into a cut portion provided in a part of the U-D bending control knob 105. The knob 105 is fitted onto the U-D rotary shaft 110 with the cut portion being aligned with the rivet 116, and the knob 105 is clamped down by a retaining member 119. An outer end portion of the U-D rotary shaft 110 has a non-circular (e.g., square) cross-sectional configuration. An auxiliary U-D bending control knob 117 for up and down bending control is fitted onto the outer end portion of the U-D rotary shaft 110. The reference numeral 118 denotes the engagement portion of the control knob 117. The configuration of the bore that is formed in the center of the auxiliary U-D bending control knob 117 is coincident with the non-circular cross-sectional configuration of the outer end portion of the U-D rotary shaft 110. Accordingly, the auxiliary U-D bending control knob 117 rotates together with the U-D rotary shaft 110 in one unit, but the control knob 117 can be removed from the U-D rotary shaft 110 by pulling it outward (i.e., upward as viewed in FIG. 4) along the axis of rotation of the knob 117.

A retaining member 119 that clamps the U-D bending control knob 105, and also prevents rotation of a disk-shaped partition 120 relative to the control knobs 105 and 117, is disposed between the U-D bending control knob 105 and the auxiliary U-D bending control knob 117 and in threaded engagement with the outer periphery of the U-D rotary shaft 110. The disk-shaped partition 120 is fitted between the retaining member 119 and the auxiliary U-D bending control knob 117. The partition 120 is formed from an elastic material which is non-permeable to water, for example, a synthetic rubber material, and has an outer diameter larger than any of the bending control knobs. It should be noted that the configuration of the partition 120 is not necessarily limited to a disk-shaped and that the partition 120 may have any desired configuration, provided that it has a larger outer diameter than any of the bending control knobs.

The partition 120 is engaged with a recess 119a formed in the retaining member 119 so that it rotates together with the U-D bending control knob 105 and the auxiliary U-D bending control knob 117 as one unit. The partition 120 is formed in the shape of an umbrella so as to cover the U-D bending control knob 105 completely. The outer peripheral edge of the partition 120 is curled in the shape of a J in cross-sectional view over the entire periphery so that contaminative matter, for example, mucus or blood, attached to the outer surface of the partition 120 will be collected in the curled edge portion. The reference numeral 120a denotes a reservoir where contaminative matter is collected.

The R-L bending control knob 106 rotates together with the R-L rotary shaft 108 through a non-circular (e.g., square) engagement portion 121 of the control knob 106, but the knob 106 can be removed by pulling it outward along the axis of rotation of the knob 106.

A clamping knob (attaching and removing means) 130 is in thread engagement with the head portion of the R-L rotary shaft 108, the knob 130 projecting upward beyond the upper end of the R-L bending control knob 106 so that the knob 130 can be rotated by hand. By manually tightening the clamping knob 130, the R-L bending control knob 106 is pressed from the outer side and thereby secured to the R-L rotary shaft 108. Thus, the auxiliary U-D bending control knob 117 and the partition 120 are simultaneously secured to the U-D rotary shaft 110. If the clamping knob 130 is untightened by hand and removed from the R-L rotary shaft 108, the R-L bending control knob 106, the auxiliary U-D bending control knob 117 and the partition 120 can be pulled outward together and thus removed from the control part 104.

A resilient friction member 131 is loaded within the large-diameter portion at the top of the R-L rotary shaft 108 in a compressed state between the rotary shaft 108 and the fixed shaft 107. Accordingly, as the R-L rotary shaft 108 rotates, frictional resistance occurs between the same and the fixed shaft 107. Therefore, the R-L bending operation is conducted while being braked with a predetermined level of frictional force at all times. The degree to which the resilient friction member 131 is compressed can be adjusted by varying the degree to which nuts 132a and 132b are screwed into the outer end portion of the R-L rotary shaft 108. The reference numeral 133 denotes a bolt screwed into the top portion of the fixed shaft 107 to prevent the R-L rotary shaft 108 from inadvertently being outwardly removed.

Although a mechanism 150 for braking the U-D bending control operation is provided between the U-D bending control knob 105 and the control part 104, description thereof is omitted. O-rings 134 to 138 for sealing are fitted to the sliding portions of the shafts to maintain the control part 104 in a water-tight condition.

In actual use of the foregoing endoscope bending control device of this embodiment, the U-D bending control knob 105 may be actuated with the doctor's left thumb, while the R-L bending control knob 106 and the auxiliary U-D bending control knob 117 may be actuated with his right hand, as shown in FIG. 5. The space on the right-hand side and the space on the left-hand side are completely isolated from each other by means of the partition 120, and any contaminative matter carried by the doctors right hand collects on the outer (right-hand) side of the partition 120 and then gathers in the reservoir 120a. Thus, there is no fear of contaminative matter attaching to the inner (left-hand) side of the partition 120.

After the use, if clamping knob 130 is untightened and removed from the R-L rotary shaft 108, the R-L bending control knob 106, the auxiliary U-D bending control knob 117 and the partition 120 can be removed for washing and disinfection or for replacement with those which have already been disinfected. It should be noted that the partition 120, which is formed from an elastic material, is flexible and fits in with the doctor's hand during a bending control operation and therefore will not interfere with the control operation. Since the partition 120 is flexible, the retaining member 119 can be held and untightened through the partition 120 from the outer side thereof, if necessary. Thus, the U-D bending control knob 105 can be removed without being contaminted.

FIG. 6 shows a third embodiment of the present invention, in which both the U-D bending control knob 105 and the R-L bending control knob 106 are provided at the outer (right-hand) side of the partition 120 in such a manner that all of them can be attached and removed as desired. By virtue of this arrangement, the doctor's left hand cannot touch any of the bending control knobs 105 and 106 and it is therefore possible to prevent contamination of the control part 104 which may occur when handling the bending control knobs 105 and 106.

FIG. 7 shows a fourth embodiment of the present invention, in which the U-D bending control knob 105 and the R-L bending control knob 106 are provided so as to be actuated with the doctor's left hand and the partition 120 and an auxiliary R-L bending control knob 126 is detachably provided at the outer (right-hand) side of the R-L bending control knob 106. With this arrangement, both the U-D bending control knob 105 and the R-L bending control knob 106 are isolated from the doctor's right hand, thereby protecting the control part 104 from contamination.

Thus, the partition 120 is only required to be disposed closer to the control part 104 than the one of the bending control knobs that is farthest from the control part 104.

According to the present invention, the space where at least one bending control knob is touched with the doctor's right hand and the space where the control part is touched with his left hand are completely isolated from each other by the partition means. Therefore, no contaminative matter carried by the right hand will attach to the control part which is on the inner (left-hand) side of the partition means, and contamination of the control part is prevented. Accordingly, there is no fear of bacteria or viruses being transmitted from one patient to another through use of the endoscope. Thus, the arrangement of the present invention is considerably superior from a hygienic point of view. Since the partition means and the one or more bending control knobs that are disposed outside of it can be removed for disinfection or replacement with others which have already been disinfected, it is unnecessary to disinfect the main body of the control part by, for example, dipping. It is therefore possible and practical to speedily carry out endoscopic diagnosis of a large number of patients with use of only one endoscope. In addition, the referred maintenance is minimized.

While the invention has been described by reference to specific embodiments chosen for purposes of illustration, it should be apparent that numerous modifications could be made thereto by those skilled in the art without departing from the basic concept and scope of the invention.

We claim:

1. A bending control device of an endoscope for bending a bendable portion, formed at the distal end of an insert part of the endoscope, by manual operation of a control part connected to the proximal end of said insert part, comprising:
   an up and down bending control knob rotatably and detachably provided on said control part to control ending of said bendable portion in upward and downward directions;
   a right and left bending control knob rotatably and detachably provided on said control part, in coaxially superposed relation to said up and down bending control knob, to control ending of said bendable portion in rightward and leftward directions; and
   a single attaching and removing means for manually attaching and removing both of said bending control knobs to and from said control part.

2. A bending control device of an endoscope according to claim 1, wherein said up and down bending control knob and said right and left bending control knob are disposed so as to be slidable along an axis of rotation of said control knobs.

3. A bending control device of an endoscope according to claim 2, wherein said attaching and removing means is a clamping knob which is in threaded engagement with a shaft of the coaxially superposed bending control knobs, whereby by tightening said clamping knob, said up and down bending control knob and said right and left bending control knob are secured to said control part, whereas, by loosening said clamping knob, said up and down bending control knob and said right and left bending control knob can both be removed from said control part.

4. A bending control device of an endoscope for bending a bendable portion, formed at the distal end of an insert part of the endoscope, by manual operation of a control part connected to the proximal end of said insert part, comprising:
   at least one up and down bending control knob rotatably provided on said control part to control bending of said bendable portion in upward and downward directions;
   at least one right and left bending control knob rotatably provided on said control part, in coaxially superposed relation to said up and down bending control knob, to control bending of said bendable portion in rightward and leftward directions; and
   partition means having a larger outer diameter than said up-and-down and said right-and-left bending control knobs, said partition means being disposed closer to said control part than the one of said bending control knob that is furthest from said control part, thereby isolating the space on the side of said partition means closest to said control part from the space on the side of said partition means furthest from said control part.

5. A bending control device of an endoscope according to claim 4, wherein said partition means is formed from an elastic material which is non-permeable to water.

6. A bending control device of an endoscope according to claim 4, wherein said partition means has a reservoir, formed along the outer peripheral edge of said partition means, for collecting contaminative matter.

7. A bending control device of an endoscope according to claim 4, wherein said partition means is in the form of a disk.

8. A bending control device of an endoscope according to claim 4, wherein said partition means, and all said bending control knobs disposed on the side of said partition means which is farthest from said control part, are detachably provided on said control part.

9. A bending control device of an endoscope according to claim 8, further comprising attaching and removing means for manually attaching and removing said partition means and said bending control knobs, to and from said control part.

10. A bending control device of an endoscope according to claim 8, wherein said partition means and bending control knobs, which are detachably provided, are disposed so as to be slidable along the axis of rotation of the knobs.

11. A bending control device of an endoscope according to claim 10, wherein said attaching and removing means is a clamping knob which is in threaded engagement with a shaft of the detachably provided bending control knobs, so that, by tightening said clamping knob, said detachably provided partition means and bending control knobs are attached to said control part, whereas, by loosening said clamping knob, the detachably provided partition means and bending control knobs may be removed from said control part.

12. A bending control device of an endoscope according to claim 4, wherein, one of said up-and-down and right-and-left bending control knobs, is disposed at the side of said partition means which is closer to said control part and the remaining bending control knobs are disposed at the side of said partition means which is farthest from said control part.

13. A bending control device of an endoscope according to claim 4, wherein all of said up-and-down and right-and-left bending control knobs are disposed at the side of said partition means which is farthest from said control part.

14. A bending control device of an endoscope according to claim 4, wherein, among the up-and-down and right-and-left bending control knobs, either an up and down bending control knob or a right and left ending control knob is disposed at the side of said partition means which is farthest from said control part and the remaining bending control knobs are disposed at the side of said partition means which is closer to said control part.

15. A bending control device of an endoscope for bending a bendable portion, formed at the distal end of an insert part of the endoscope, by manual operation of a control part connected to the proximal end of said insert part, comprising:

a bending control knob rotatably provided on said control part to control bending of said bendable portion; and partition means having a larger outer diameter than said bending control knob, said partition means being disposed closer to said control part than said ending control knob, thereby isolating the space at the side of said partition means which is closer to said control part from the space at the side of said partition means where said bending knob is located.

* * * * *

UNITED STATES PATENT AND TRADEMARK OFFICE
CERTIFICATE OF CORRECTION

PATENT NO. : 5,007,406
DATED : April 16, 1991
INVENTOR(S) : Nagashige TAKAHASHI

It is certified that error appears in the above-indentified patent and that said Letters Patent is hereby corrected as shown below:

. On the cover page, item [56], change "4,462,282" to ---4,461,282---.

Signed and Sealed this

Twenty-first Day of February, 1995

Attest:

BRUCE LEHMAN

Attesting Officer     Commissioner of Patents and Trademarks